US012678216B2

(12) United States Patent (10) Patent No.: US 12,678,216 B2
Batchelor et al. (45) Date of Patent: Jul. 14, 2026

(54) INDUCTIVE POWER JOINT ALLOWING UNRESTRICTED ROTATION

(71) Applicant: GYRUS ACMI, INC., Southborough, MA (US)

(72) Inventors: Kester Julian Batchelor, Mound, MN (US); Theodore C. Blus, Arden Hills, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 556 days.

(21) Appl. No.: 17/128,442

(22) Filed: Dec. 21, 2020

(65) Prior Publication Data

US 2021/0186591 A1 Jun. 24, 2021

Related U.S. Application Data

(60) Provisional application No. 62/952,966, filed on Dec. 23, 2019.

(51) Int. Cl.
A61B 18/14 (2006.01)
A61B 18/00 (2006.01)

(52) U.S. Cl.
CPC .............................. A61B 18/1445 (2013.01); *A61B 2018/00202* (2013.01); *A61B 2018/00208* (2013.01); *A61B 18/1482* (2013.01)

(58) Field of Classification Search
None
See application file for complete search history.

(56) References Cited

U.S. PATENT DOCUMENTS

| | | | | |
|---|---|---|---|---|
| 5,849,020 | A | * 12/1998 | Long | A61B 18/1447 |
| | | | | 606/167 |
| 8,808,283 | B2 | 8/2014 | Moua et al. | |
| 10,278,770 | B2 | 5/2019 | Kerr | |
| 10,349,963 | B2 | 7/2019 | Fiksen et al. | |
| 2013/0073021 | A1* | 3/2013 | Halperin | G01R 33/3685 |
| | | | | 607/116 |
| 2014/0005681 | A1* | 1/2014 | Gee | A61B 34/71 |
| | | | | 606/130 |

(Continued)

FOREIGN PATENT DOCUMENTS

WO    WO-2021133728 A1    7/2021

OTHER PUBLICATIONS

"International Application Serial No. PCT/US2020/066402, International Search Report mailed Apr. 14, 2021", 5 pgs.

(Continued)

*Primary Examiner* — Joanne M Rodden
*Assistant Examiner* — Nora W Rhodes
(74) *Attorney, Agent, or Firm* — Schwegman Lundberg & Woessner, P.A.

(57) ABSTRACT

A user-held or otherwise supported electrosurgical device can include an endpiece, a fixed first coil or other electromagnetic energy transmitter or receiver and a rotatable second coil or other electromagnetic energy transmitter or receiver wirelessly energized by the first coil. The rotatable second coil can be affixed to a rotatable member extending distally from the endpiece. This can permit unrestricted rotation without being encumbered by wiring or electrical contacts across a plane of rotation.

23 Claims, 6 Drawing Sheets

(56) References Cited

U.S. PATENT DOCUMENTS

2015/0209035 A1*  7/2015  Zemlok ............ A61B 17/07207
                                                  73/1.01
2015/0359565 A1   12/2015  Matsui
2017/0332881 A1*  11/2017  Matsuki ............. A61B 17/0218
2018/0212451 A1    7/2018  Schmidt et al.
2018/0247759 A1*   8/2018  Fuller ...................... A61C 3/02
2019/0247141 A1    8/2019  Batchelor et al.

OTHER PUBLICATIONS

"International Application Serial No. PCT/US2020/066402, Written Opinion mailed Apr. 14, 2021", 6 pgs.
"International Application Serial No. PCT/US2020/066402, International Preliminary Report on Patentability mailed Jul. 7, 2022", 8 pgs.

* cited by examiner

600

602
INSERT A HANDHELD ELECTROSURGICAL DEVICE INTO A BODY OF A PATIENT

604
ACTIVATE AN END EFFECTOR LOCATED AT A DISTAL PORTION OF A ROTATABLE MEMBER

606
ROTATE THE ROTATABLE MEMBER

INDUCTIVE POWER JOINT ALLOWING UNRESTRICTED ROTATION

CROSS-REFERENCE TO RELATED APPLICATION

This application claims the benefit of priority to U.S. Provisional Patent Application Ser. No. 62/952,966, filed on Dec. 23, 2019, the contents of which are incorporated herein in their entirety.

TECHNICAL FIELD

The present disclosure relates to electrosurgical medical devices.

BACKGROUND

Electrosurgery involves various techniques that can be used during medical procedures, such as, for example, laparoscopic surgery. The techniques may include, for example, cutting, clamping, coagulating, desiccating, fulgurating, or the like, of biological tissue. These techniques may be used in procedures such as, for example, appendectomies, cholecystectomies, colectomies, cystectomies, gastric banding, gastric bypass, hernia repair, nephrectomy, Nissen fundoplication, prostatectomies, sleeve gastrectomy, or other similar procedures.

During electrosurgery, an electrosurgical signal can be generated by an electrosurgical generator and provided to the biological tissue through an electrosurgical device. The electrosurgical energy can be provided to tissue via an end effector of the electrosurgical device. The end effector may include, for example, forceps, a conductive spatula, a j-hook, electrical pads, or the like. Different medical procedures can use different electrosurgical signals so as to achieve results specific to these different medical procedures. Various electrical metrics of the electrosurgical signal provided to the biological tissue being treated can be used to characterize the electrosurgical signal. These electrical metrics can include: polarity (e.g., monopolar, bipolar), AC and/or DC, frequency, signal amplitude, attack and decay profiles, pulse width, duty cycle, or the like. Depending on the medical procedure and the end effector being used, a surgeon may be required to manipulate the device in order to move (e.g., reposition or relocate) the end effector within the body of a patient to achieve a desired outcome or result during the surgery.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
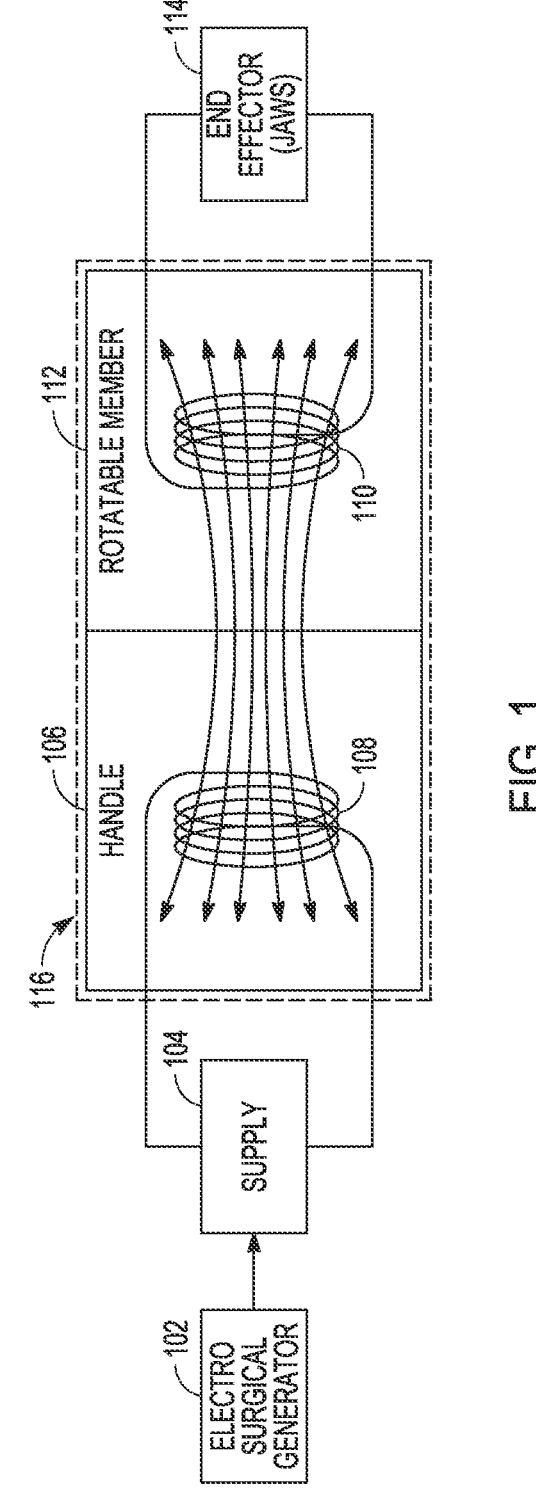
FIG. 1 illustrates an example of a system for a user-held or otherwise supported electrosurgical device.

Electrosurgery can involve the manipulation of biological tissue using a distal end effector, such as a forceps, a conductive spatula, a j-hook, electrical pads, or the like, of an electrosurgical device. The treatment of the tissue can involve applying an electrosurgical or other electrotherapeutic signal, such as to produce a change in biological tissue of a surgical patient in some manner. Energy delivered at or near the end effector can be used to modify the biological tissue such as via localized heating, coagulation or desiccation of the tissue, changing the structure of the tissue, or destruction of the tissue at the cellular level. The tissue can be modified, for example, by electrical arc strikes emitted by the electrosurgical device at the end effector, by heating the end effector, or the like, alone or in combination with mechanical tissue manipulation such as grasping, cutting, or the like. The medical procedure may have one or more electrotherapeutic phases, such as, for example, an interrogation phase, a heating phase, a drying phase, a cauterizing phase, or the like.

The electrosurgical generator can be programmed to produce a specified electrical waveform, which can be selected from a variety of electrical waveforms, such as to obtain a desired corresponding tissue effect, such as one or more of those described herein. The electrosurgical generator can be connected via a cord, having electrical conductors, to a handle, housing or other endpiece of a user-held or otherwise supported electrosurgical medical instrument, such as to permit the therapeutic electrical signal to be passed from the handpiece or other endpiece via a shaft to an end effector and ultimately to the tissue.

One approach for passing the electrical signal is using one or more pairs of electrical contacts that transfer power from a transducer to the handle or other endpiece and via the shaft to the end effector. However, the contacts may tarnish or may otherwise create an unwanted resistance, which, in turn, may create localized heat points, or may otherwise interfere with delivering the electrosurgical signal waveform, such as by causing a signal loss). Furthermore, ingress of fluid (e.g., blood, water, saline, or the like) may also prevent contacts from functioning properly, such as by creating an unintended electrical conduction path between different individual pairs of contacts.

Another approach of passing the electrosurgical signal from the handle or other endpiece to the end effector is via electrically conductive wires that span the entire length of the instrument from the handle or other endpiece, through an elongated shaft, and to the end effector. During a medical procedure, a surgeon may desire to rotate the end effector and shaft with respect to the handpiece, housing, or other endpiece. Such rotation can be impeded by the electrical conductors extending along the shaft and across the plane of rotation. This can limit the amount of rotation (e.g., to 180 degrees or to 330 degrees). Such a rotational limitation may cost a surgeon extra time to reposition the end effector to cause the end effector to be positioned correctly for the medical procedure being performed. For example, when the rotation runs up against the electrical conductor, the surgeon may have to rotate the shaft and end effector in the opposite direction in order to achieve the desired rotational orientation of the end effector.

The present inventors have recognized, among other things, that such a rotational limitation can be overcome by using a coil or other inductive or other electromagnetic energy transmitter located in the handle or other endpiece and a second, separate coil or other inductive or other electromagnetic energy receiver that rotates with the shaft or other rotatable member that is rotatably attached to the handle or other endpiece. This can help allow for unrestricted rotation of the end effector via the shaft and can also help avoid issues caused using movable electrical contacts.

For example, an instrument handle or other endpiece may include a first coil or other inductive or other electromagnetic energy transmitter or receiver. A rotatable shaft or other rotatable member, including a proximal portion and a distal portion, can be rotatably coupled to the handle or other endpiece at its proximal portion. The rotatable member may include a second coil or other inductive or other electromagnetic energy transmitter or receiver, such as can be arranged with respect to the first coil or other inductive or other electromagnetic energy transmitter or receiver to permit wireless electromagnetic energy transfer therebetween. The wireless inductive or other electromagnetic energy transfer can be permitted during rotation of the rotatable member with respect to the handle or other endpiece, such as without impeding such rotation by being constrained by wires extending across a plane of rotation between the handle or other endpiece and the rotatable member.

FIG. 1 illustrates an example of an electrosurgical system 100. The system 100 can include an electrosurgical generator 102. The electrosurgical generator 102 can be electrically connected or coupled to handheld (or machine supported) electrosurgical instrument 116. The electrosurgical instrument 116 can include an endpiece support such as a handle, housing, or handpiece 106, such as can be held by a user or supported by a robotic apparatus or other machine. The handle 106 or other endpiece support can be coupled to a shaft or other rotatable member 112 that is rotatable with respect to the handle 106 or other endpiece. An end effector 114 can be located at a distal portion or tip of the rotatable member 112.

An inductive first coil 108 or other electromagnetic energy transmitter can be fixed within the handle 106 or other endpiece. The first coil 108 can be electrically connected to the electrosurgical generator 100 or to an intermediate power supply 104. An inductive second coil 110 or other electromagnetic energy receiver can be fixed to the rotatable member 112 of the electrosurgical instrument 116. The second coil 110 can rotate with the rotatable member 112, such as coaxially with respect to the first coil 108. In this way, energy can be transmitted from the first coil 108 to the second coil 110, such as via a coupled magnetic field therebetween-including during rotation of the rotatable member 112 with respect to the handle 106 or other endpiece.

An alternating current (AC) or other electrosurgical input signal from the electrosurgical generator 102 can be communicated directly across the first coil 108 and the second coil 110, such as via the inductive coupling therebetween. When a direct current (DC) signal is desired at the end effector (e.g., for lighting or electroporation), the AC signal received at the second coil 110 can be communicated to demodulator circuitry coupled thereto, such as to demodulate the AC signal into a DC signal that can be provided to or toward the end effector 114.

The first coil 108 and the second coil 110 can be located concentric to a shared central longitudinal axis. The first coil 108 and the second coil 110 can be located concentric to each other, either axially displaced from each other or, if desired, one inside the other. In an example, a coaxial axis can be the axis of the rotatable member 114 which can be a longitudinal tube or other elongated shaft.

By selecting a winding ratio other than 1:1, such an arrangement may allow the first coil 108 and the second coil 110 to act as a step-up or step-down transformer, such as to step up or step down the electrosurgical signal (e.g., a voltage or current) from the electrosurgical generator 102 the effector 114.

The end effector 114 may include one or more of: a blade, which may include an electrosurgical blade, a forceps, a jaw member, a surgical spatula, a j-hook, a needle, or the like. The end effector 114 may additionally or alternatively include an electrode or a pin (or array of pins) such as to provide electrosurgical energy such as to treat tissue. Energy at the end effector 114 can be used to modify tissue by, for example, localized heating, desiccation, cutting, coagulation, changing the structure of the tissue, or the like. Such tissue modification can be performed using electrical arc delivered to the tissue and, depending upon the particular type of tissue modification desired, may involve a different amount of current, voltage, power, or the like, delivered to the tissue at the end effector 114.

In an example, tissue can be modified by passing an AC signal through the tissue from a first jaw electrode located on a first jaw member to a second jaw electrode located on a second jaw member with the tissue located between the first and second jaw members, such as when tissue is being grasped or gripped between the jaw members of a surgical forceps. Resistance in the tissue may give rise to internally generated heat within the tissue, which leads to modification of the tissue.

In another example, an AC signal can be delivered to an ultrasonic transducer placed on the rotatable member 112. The ultrasonic transducer may in turn, create mechanical vibrations that propagate to the end effector 114 and produce heat in, and thus modify, the tissue due to frictional heating.

In an example, power level at the end effector 114, may range from 2 watts to 400 watts (W). Similarly, current at the end effector 114 may range from 100 milli-amperes (mA) to 7 amperes (A), and voltage may range from 0.5 volts (V) to 400 V. The amount of power, current, or voltage delivered at the end effector 114 may depend on one or more factors such as the amount of fluid (e.g., blood, water, saline, or the like) in the area of the tissue being affected. For example, if there is more fluid in the affected area, more power, more current, but less voltage can be useful to heat the tissue.

The amount of power, current, or voltage delivered at the end effector 114 may also depend on whether the end effector 114 is configured and operated in a monopolar or bipolar configuration. A bipolar end effector can include closely-spaced first and second electrodes (e.g., located in a space between the arms or jaws of an electrosurgery forceps of the end effector 114). A monopolar configuration can include a first electrosurgical electrode located at the end effector 114 and a more distant separate second electrosurgical electrode (e.g., the second electrosurgical electrode can be electrically attached to the patient, such as by providing an electrically conductive pad electrode that can be placed under the patient).

In a bipolar forceps configuration, an amount of tissue between electrodes may involve less voltage to drive enough current to affect the tissue as desired. In a monopolar forceps configuration, more voltage can be involved to drive a smaller current to affect the tissue as desired.

Figure 2:
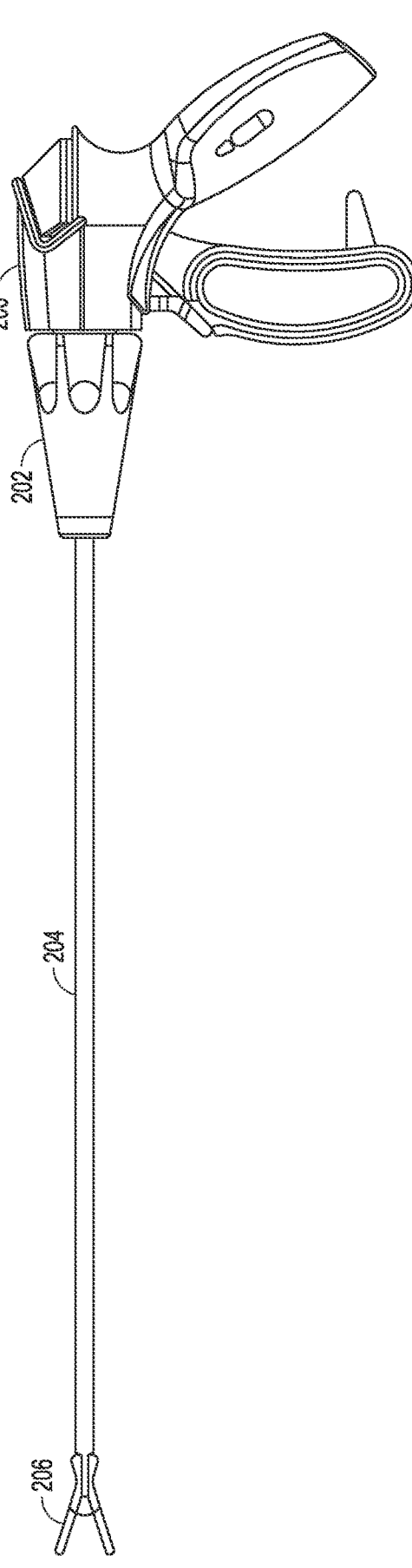
FIG. 2 illustrates an example of a user-held or otherwise supported electrosurgical device.

FIG. 2 illustrates an example of a user-held or otherwise supported electrosurgical device. The electrosurgical device may include a handle, endpiece, housing, or handpiece 200 connected to a rotatable shaft or other rotatable member 204. The rotatable member 204 may include a rotatable nose portion 202 on the rotatable member 204, such as adjacent to the handle 200 or other endpiece. The rotatable member 204 may extend distally from a rotatable nose portion 202 that can surround and can be connected to a proximal portion of the rotatable member 204. The rotatable nose portion 202 can be rotated with respect to the handle 200 or other endpiece. The rotatable nose portion 202 can be rotated manually by the user, such as while holding the handle 200 or other endpiece. The rotatable nose portion 204 can be connected to a powered bidirectional rotational actuator that can be triggered at the handle 200 or other endpiece while holding the handle 200 or other endpiece, such as by pushing a button on the handle 200 or other endpiece. The rotatable nose portion 202 can be entirely eliminated from the electrosurgical device. The rotatable nose portion 202 can be replaced by a rotatable wheel located in (and partially protruding from) the handle 200 or other endpiece, such as shown and described with respect to FIG. 5, below.

Figure 3:
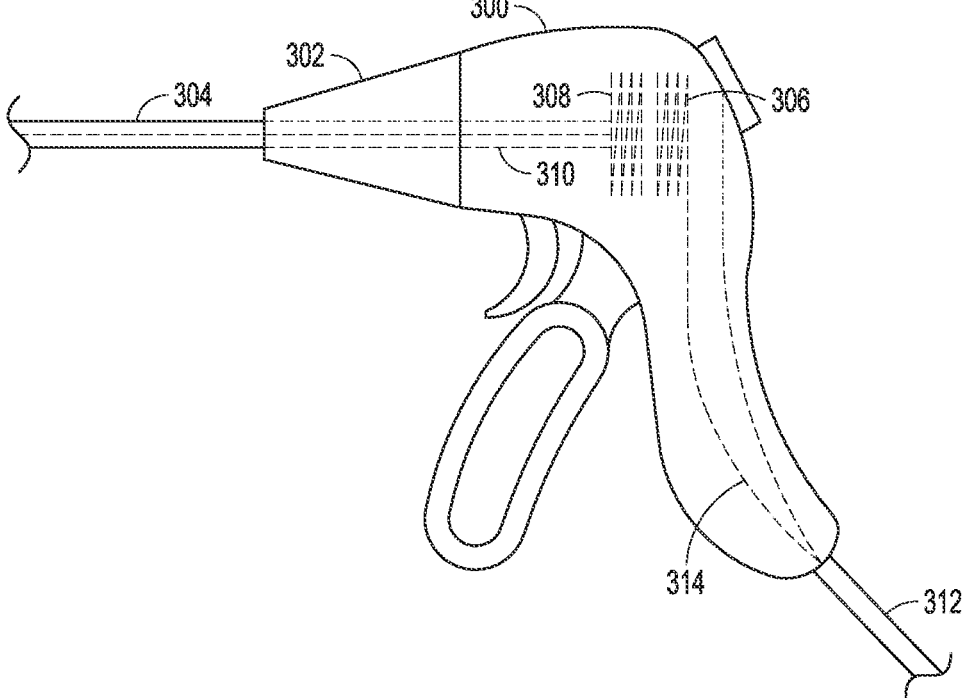
FIG. 3 illustrates an example of a user-held or otherwise supported electrosurgical device showing an example location of coils within a handpiece or other endpiece.

FIG. 3 illustrates an example of a user-held or otherwise supported electrosurgical device showing an example of location of power transmitter and power receiver coils within a handle, endpiece, housing, or handpiece 300. In an example, the handle 300 or other endpiece can house a "transmitter" first coil 306 and a "receiver" second coil 308 within the interior of the handle 300 or other endpiece. The first coil 306 can be electrically coupled to an electrosurgical generator 102, such as via electrical conductors in a cord 312, such as a power cord or other electrically conducting wire, connected to the handle 300 or other endpiece. The second coil 308 can be electrically coupled to an end effector 114, 206, such as via electrical conductors in a cord or electrically conducting wire 310 extending through a rotatable nose portion 302, through an elongated shaft or other rotatable member 304, a distal portion of which is coupled to the end effector 114, 206.

In FIG. 3, the first coil 306 may energize the second coil 308 via a mutual inductance therebetween, such as to allow electromagnetic energy to be transferred from the electrosurgical generator 102, to an end effector 114, 206. In FIG. 3, the second coil 308 can be affixed to and rotatable with the rotatable nose portion 302 and electrically connected to an end effector 114, 206 such as by electrical conductors within a cord or other electrically conducting wire 310. In FIG. 3, the arrangement and wiring of the first coil 306 and the second coil 308 need not include electrical wires extending across the plane of rotation between the rotatable member 304 and the handle 300 or other endpiece. This can allow for unlimited rotation of the elongated shaft or other rotatable member 304, such as by turning the rotatable nose portion 302.

For example, an electrically conducting wire 314, may connect cord 312 to the first coil 306 as described above. Similarly, cord 310 can be connected to the second coil 308 and pass energy through electrical conductors within the cord 310 to an end effector such as 114 or 206 as described above in FIGS. 1 and 2.

Figure 4A:
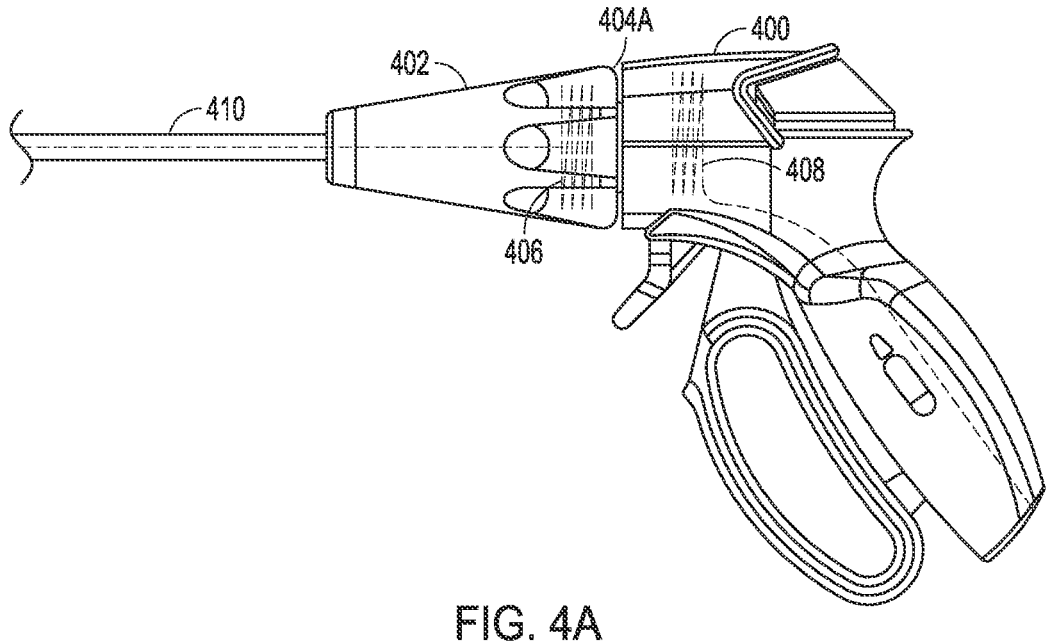
FIGS. 4A and 4B illustrate an example of a user-held or otherwise supported electrosurgical device showing a coil located within the handpiece or other endpiece and a coil in the rotatable member.
Figure 4B:
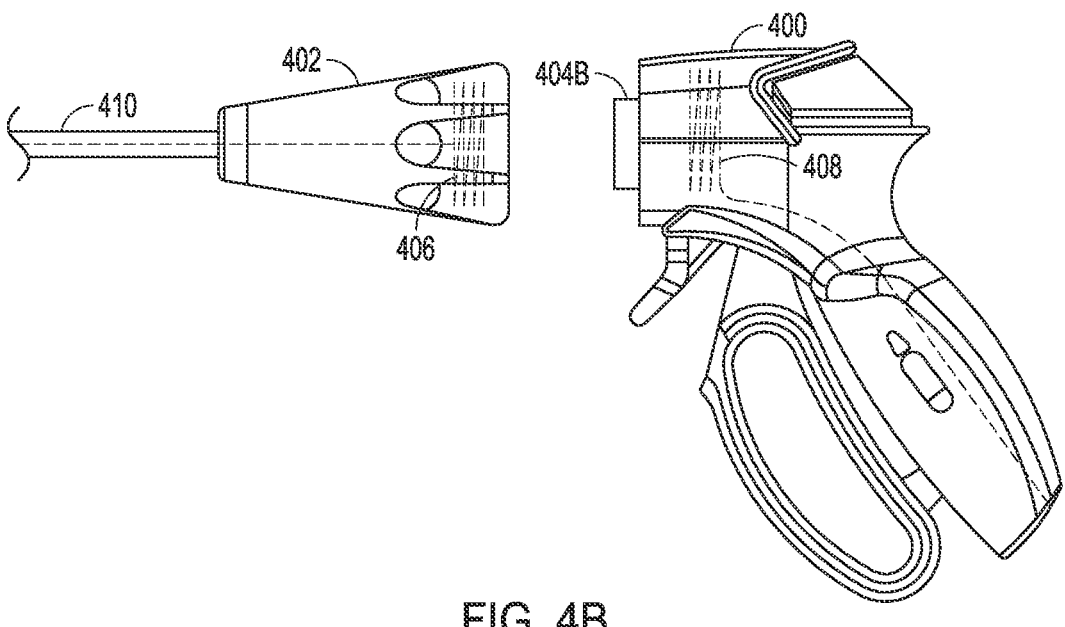

FIGS. 4A and 4B illustrate an example of a user-held or otherwise supported electrosurgical device showing a coil 408 located within the handle 400 or other endpiece and a coil affixed to the rotatable member. In FIG. 4A, the handle 400 or other endpiece and rotatable nose portion 402 can be connected at user-attachment and user-detachment location 404A at which the rotatable nose member 402 can be user-attached to or user-detached from the handle 400 or other endpiece. The sub-assembly of the rotatable nose portion 402 and the rotatable member 410 can be a single-use or disposable portion. The rotatable nose portion 402 or rotatable member 410 can be user-attached or user-detached from the handle 400 or other endpiece, such as via a user attachment/detachment actuator. The user attachment/detachment actuator can be triggered by a switch or button. Such triggering switch or button can be located on the handle 400 or other endpiece, the rotatable nose portion 402, the rotatable member 410, or elsewhere. The triggering switch or button can be engaged by the user such as to cause the handle 400 or other endpiece to connect to the rotatable nose portion 402 or to the rotatable member 410, such as at an attachment/detachment location 404B.

In an example, a power transmitting first coil 408 can be located within the handle 400 or other endpiece. The first coil 408 can be connected to an electrosurgical generator 102. In FIGS. 4A and 4B, a power-receiving second coil 406 can be located in the rotatable nose portion 402, such as to wirelessly receive energy from the first coil 408 and to provide energy via the rotatable member 410 to the end effector 114, 206. In an example, the second coil 406 can be included in or on the elongated shaft or other rotatable member 410. Thus, detaching the rotatable nose portion 402 from the handle 400 or other endpiece can separate the second coil 406, the rotatable member 410, and the end effector 114, 206, which can be disposed of, from the handle 400 or other endpiece and the first coil 408.

The first coil 408 may wirelessly energize the second coil 406, which can, in turn, provide energy to an end effector 114, 206. In FIGS. 4A and 4B, the second coil 406 can be affixed to the rotatable portion 410 and to the end effector 114, 206. Electrical conductors within a cord 310 can provide energy received by the second coil 406 to the end effector 114, 206. In FIGS. 4A and 4B, the arrangement of the first coil 408 and the second coil 406 need not require wiring therebetween. This can help allow for unlimited rotation of the rotatable member (e.g., an elongated shaft) 410, such as by turning the rotatable nose portion 402. Such an arrangement allows unlimited rotation of a wire in the handle 400 or other endpiece, such as 314 as described above, relative to a wire in the rotatable portion 410 connected to an end effector 114, 206, such as 310 as described above so as to keep the wire in the handle 400 or other endpiece and a wire in the rotatable portion from twisting or winding together and causing one, the other, or both from rupturing.

Figure 5:
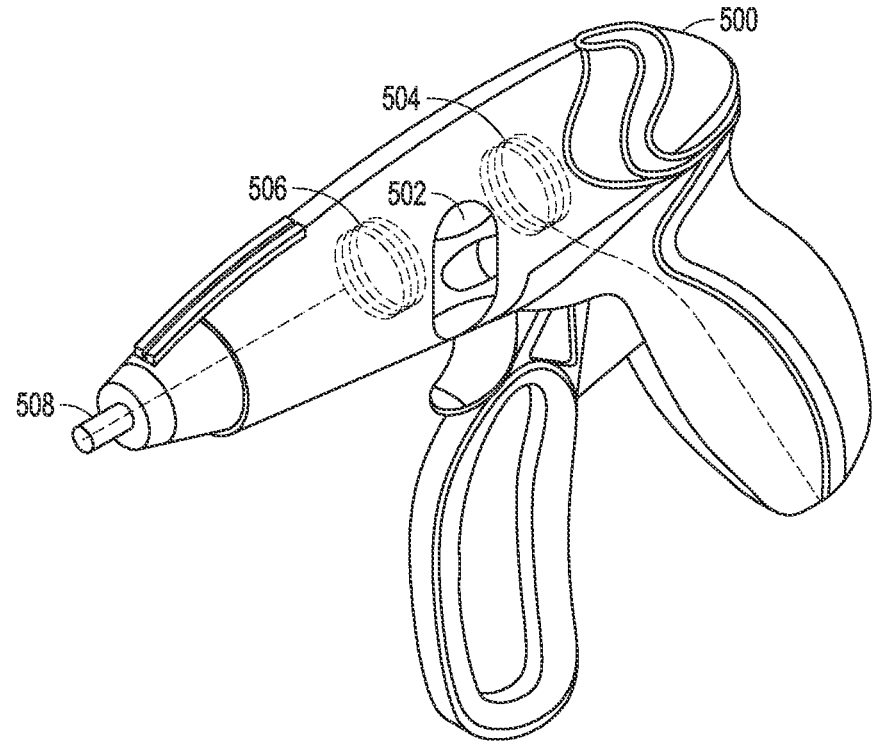
FIG. 5 illustrates an example of a user-held or otherwise supported electrosurgical device in which the rotatable member includes a wheel.

FIG. 5 illustrates an example of a user-held or otherwise supported electrosurgical device 500 having a proximal portion and a distal portion, and in which the rotatable member can include a wheel or other rotational portion 502. The rotatable wheel can be located between the proximal portion and the distal portion of the device 500. A power-transmitting first coil 504 can be located in the proximate portion of the device 500, and a power-receiving second coil 506 can be located in the distal portion of the device 500.

The first coil 504 can be electrically connected to an electrosurgical generator 102 by an electrically conducting wire 314 connected to a cord such as 312, and the second coil 506 can be electrically connected to an end effector 114, 206. In FIG. 5, the first coil 504 may wirelessly energize the second coil 506, such as to allow transfer energy from the electrosurgical generator 102 to an end effector 114, 206. The second coil 506 can be affixed to the rotatable portion 502 and affixed to and electrically connected to an end effector 206 such as by electrical conductors in a cord 310. In FIG. 5, the arrangement of the first coil 504 and the second coil 506 need not require any electrical wiring therebetween which can help allow for unlimited rotation of the elongated shaft or other rotatable member 508 such as by turning the rotatable portion 502.

Figure 6:
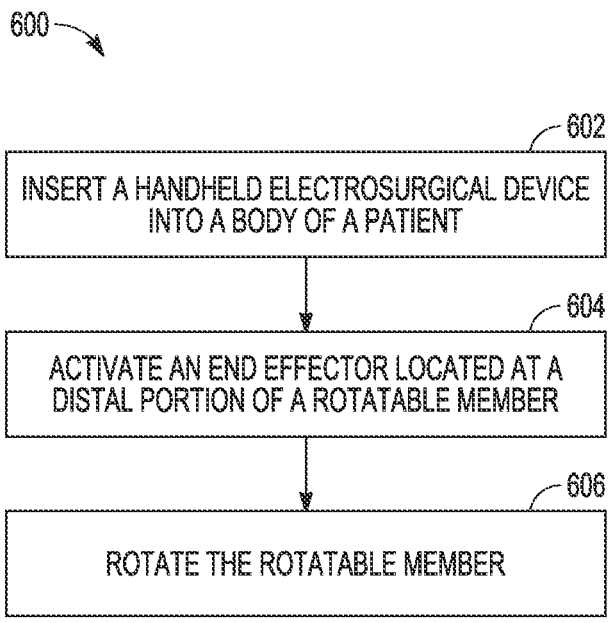
FIG. 6 illustrates an example comprising a technique, such as a method for using a medical apparatus.

FIG. 6 illustrates an example of a technique or method for using a medical apparatus. At 602, a user-held or otherwise supported electrosurgical device can be partially inserted into the body of a patient. Specifically, the distal end of an elongated shaft or other rotatable member having a distal end including an end effector, can be inserted into the patient, such as via a trocar, a cannula, or the like. In an example, an end effector on the distal end of a rotatable member can be used during open surgery, laparoscopic surgery, or other medical procedure.

At 604, the end effector can be activated. The activation may include, grasping tissue with a forceps, cutting tissue with a blade or an electrode, heating or desiccating tissue, changing or transforming a state of tissue, or the like. The activation may also include providing, transmitting, or the like, electrical energy to the end effector.

At 606, the elongated shaft or other rotatable member can be rotated. Rotation may involve turning a rotatable nose portion, wheel, dial, or the like of the rotatable member such as to cause the rotatable member to rotate in an unrestricted manner.

As described in the various examples herein, either or both of the first coils 108, 306, 408, 504 or the second coils 110, 308, 406, 506 can be potted, filled, coated encapsulated or the like to protect the coils 108, 110, 306, 308, 406, 408, 504, or 506 from elements or factors such as moisture (e.g., liquid/fluid ingress), vibration, or extremes in current, voltage, power or temperature levels which may damage or degrade, or otherwise affect the performance of the coils 108, 110, 306, 308, 406, 408, 504, or 506. The potting can be accomplished using a solid or gelatinous substance (e.g., a thermosetting plastic, silicon rubber, epoxy resin, or the like).

The above detailed description includes references to the accompanying drawings, which form a part of the detailed description. The drawings show, by way of illustration, specific embodiments that can be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A medical apparatus comprising:
an electrosurgical device comprising:
an endpiece including a first electromagnetic energy transmitter or receiver;
an elongate shaft including a proximal portion and a distal portion; and
a rotatable member including a proximal portion and a distal portion, the proximal portion of the rotatable member being rotatably coupled to the endpiece and the distal portion of the rotatable member being coupled to the elongate shaft and configured to actuate rotation of an end effector, wherein the rotatable member includes a second electromagnetic energy transmitter or receiver rotatable together with the rotatable member and arranged longitudinally spaced apart from the first electromagnetic energy transmitter or receiver to permit wireless electromagnetic energy transfer therebetween including during rotation of the rotatable member with respect to the endpiece, and wherein the first electromagnetic transmitter or receiver is located entirely within the endpiece and the second electromagnetic energy transmitter or receiver is located entirely within the rotatable member, wherein the first electromagnetic energy transmitter or receiver and the second electromagnetic energy transmitter or receiver wrap around a shared central longitudinal axis and are axially displaced from one another such that the second electromagnetic energy transmitter or receiver is located distally along the shared central axis from the first electromagnetic energy transmitter or receiver, and wherein no portion of the first electromagnetic transmitter or receiver is located in or on the elongate shaft or overlaps any portion of the elongate shaft.

2. The medical apparatus of claim 1, wherein the first electromagnetic energy transmitter or receiver includes a first coil, and wherein the second electromagnetic energy transmitter or receiver includes a second coil.

3. The medical apparatus of claim 2, wherein the first coil and the second coil are coaxial to each other.

4. The medical apparatus of claim 3, wherein the rotatable member is connected to a longitudinal electrical conductor connecting to the end effector, and wherein the second electromagnetic energy transmitter or receiver is located arranged with respect to the first electromagnetic energy transmitter or receiver to permit wired electrical energy transfer between the second electromagnetic energy transmitter or receiver and the longitudinal electrical conductor.

5. The medical apparatus of claim 2, wherein the first coil and the second coil are inductively coupled to each other.

6. The medical apparatus of claim 4, wherein the first coil is arranged to be coupled to an electrosurgical energy generator, and wherein the second coil is electrically connected via the longitudinal electrical conductor to provide energy to the end effector.

7. The medical apparatus of claim 6, wherein the end effector includes a forceps.

8. The medical apparatus of claim 6, wherein the end effector includes a blade.

9. The medical apparatus of claim 6, wherein the end effector includes one or more pins.

10. The medical apparatus of claim 2, wherein at least one of the first coil or the second coil is potted.

11. The medical apparatus of claim 2, wherein the rotatable member includes a rotatable nose portion such that the elongate shaft is configured to rotate with the rotatable member, and wherein the second coil is located entirely within the rotatable nose portion and adjacent to the end-piece.

12. The medical apparatus of claim 1, wherein at least one of the endpiece or the rotatable member includes a user engagement actuator, arranged to allow at least one of user-attachment or user-detachment between the endpiece and the rotatable member.

13. The medical apparatus of claim 1, wherein the rotatable member is rotatable with respect to the endpiece unrestricted by any wiring between the rotatable member and the endpiece.

14. The medical apparatus of claim 1, wherein at least one of the first electromagnetic energy transmitter or receiver or the second electromagnetic energy transmitter or receiver includes an inductor or inductance.

15. A method of using a medical apparatus comprising:

inserting an electrosurgical device into a body, the electrosurgical device including a handle endpiece, the handle endpiece including a first electromagnetic energy transmitter or receiver, wherein the first electromagnetic energy transmitter or receiver is located entirely within the handle endpiece;

activating an end effector located at a distal portion of an elongate shaft including a longitudinal electrical conductor, wherein the elongate shaft is connected to a rotatable member, the rotatable member including a proximal portion and the distal portion, the proximal portion of the rotatable member being rotatably coupled to the handle endpiece, and the distal portion of the rotatable member being coupled to the elongate shaft, the rotatable member including a second electromagnetic energy transmitter or receiver located outside of the elongate shaft, entirely within the rotatable member, and electrically connected to the longitudinal electrical conductor of the elongate shaft, wherein the second electromagnetic energy transmitter or receiver is arranged longitudinally spaced apart and offset from the first electromagnetic energy transmitter or receiver to permit wireless electromagnetic energy transfer therebetween including during rotation of the rotatable member with respect to the handle endpiece, and wired electrical energy transfer between the second electromagnetic energy transmitter or receiver and the longitudinal electrical conductor of the elongate shaft, wherein the first electromagnetic energy transmitter or receiver and the second electromagnetic energy transmitter or receiver wrap around a shared central longitudinal axis and are axially displaced from one another such that the second electromagnetic energy transmitter or receiver is located distally along the shared central axis from the first electromagnetic energy transmitter or receiver, and wherein no portion of the first electromagnetic transmitter or receiver is located in or on the elongate shaft or overlaps any portion of the elongate shaft; and rotating the rotatable member.

16. The method of claim 15, wherein the first electromagnetic energy transmitter or receiver includes a first coil, and wherein the second electromagnetic energy transmitter or receiver includes a second coil.

17. The method of claim 16, wherein the first coil and the second coil are coaxial to each other.

18. The method of claim 16, wherein the first coil and the second coil are axially displaced from each other along a longitudinal axis of the rotatable member.

19. The method of claim 16, wherein the first coil and the second coil are inductively coupled to each other.

20. The method of claim 16, wherein the first coil is arranged to be coupled to an electrosurgical energy generator, and wherein the second coil is electrically connected via the elongate shaft to provide energy to the end effector.

21. An electrosurgical device comprising:

an elongate shaft, the elongate shaft including a longitudinal electrical conductor;

a handle endpiece;

a rotatable member attached to the elongate shaft at a first end and attached to the handle endpiece at a second end;

an electromagnetic energy transmitter located entirely within a portion of the handle endpiece, wherein the electromagnetic energy transmitter is electrically coupled to an electrosurgical generator; and an electromagnetic energy receiver located entirely within, and rotatable together with, the rotatable member, arranged longitudinally spaced apart and offset from the electromagnetic energy transmitter to permit wireless electromagnetic energy transfer therebetween including during rotation of the rotatable member with respect to the handle endpiece, and wired electrical energy transfer with a longitudinal electrical conductor of the elongate shaft, and wherein the electromagnetic energy transmitter and the electromagnetic energy receiver wrap around a shared central longitudinal axis and are axially displaced from one another such that the electromagnetic energy receiver is located distally along the shared central axis from the electromagnetic energy transmitter, and wherein no portion of the electromagnetic energy transmitter is located in or on the elongate shaft or overlaps any portion of the elongate shaft.

22. The electrosurgical device of claim 21, wherein the electromagnetic energy transmitter includes a first coil and wherein the electromagnetic energy receiver includes a second coil, wherein the second coil is electrically connected via the longitudinal electrical conductor to provide energy to an end effector located at a distal portion of the elongate shaft.

23. The electrosurgical device of claim 21, wherein the rotatable member is a rotatable nose portion connected to the elongate shaft such that the elongate shaft is configured to rotate with the rotatable member.

\* \* \* \* \*